(12) United States Patent
Jun et al.

(10) Patent No.: US 6,449,037 B2
(45) Date of Patent: Sep. 10, 2002

(54) METHOD OF AND DEVICE FOR DETECTING MICRO-SCRATCHES

(75) Inventors: Chung-sam Jun, Hwasung-gun; Sang-mun Chon, Sungnam; Sang-bong Choi; Hyung-suk Cho, both of Suwon; Pil-sik Hyun, Yongin; Kyu-hong Lim; Byung-am Lee, both of Suwon, all of (KR)

(73) Assignee: Samsung Electronics Co., Ltd., Suwon (KR)

( * ) Notice: Subject to any disclaimer, the term of this patent is extended or adjusted under 35 U.S.C. 154(b) by 0 days.

(21) Appl. No.: 09/864,398

(22) Filed: May 25, 2001

Related U.S. Application Data

(62) Division of application No. 09/584,671, filed on Jun. 1, 2000.

(30) Foreign Application Priority Data

Aug. 23, 1999 (KR) ............................................ 99-34927

(51) Int. Cl.[7] ................................................ G01N 21/00
(52) U.S. Cl. ................................ 356/237.4; 356/237.5; 356/239.2; 356/237.3
(58) Field of Search .......................... 356/237.1, 237.2, 356/237.3, 237.4, 239.1, 239.2, 239.7, 239.8, 364, 365, 366, 367, 368, 369, 370; 250/360.1

(56) References Cited

U.S. PATENT DOCUMENTS

| | | | |
|---|---|---|---|
| 4,652,757 A | * 3/1987 | Carver ..................... | 250/360.1 |
| 4,893,932 A | * 1/1990 | Knollenberg ............... | 356/369 |
| 4,957,368 A | * 9/1990 | Smith ......................... | 356/369 |
| 5,424,536 A | * 6/1995 | Moriya ....................... | 356/369 |
| 5,465,145 A | * 11/1995 | Nakashige et al. ...... | 356/237.1 |
| 5,818,576 A | 10/1998 | Morishige et al. | |
| 6,034,776 A | * 3/2000 | Germer et al. ........... | 356/237.5 |
| 6,169,601 B1 | * 1/2001 | Eremin et al. ........... | 356/239.8 |
| 6,271,961 B1 | * 8/2001 | Marxer et al. ........... | 356/237.3 |

FOREIGN PATENT DOCUMENTS

| | | |
|---|---|---|
| EP | 0 355 163 A2 | 10/1989 |
| EP | 398781 A2 | 11/1990 |
| EP | 0 530 922 A2 | 3/1993 |
| JP | 62-19739 | 1/1987 |
| JP | 1-137642 | 5/1989 |
| JP | 8-145620 | 6/1996 |
| JP | 9-89794 | 4/1997 |
| WO | WO 94/22003 | 9/1994 |
| WO | WO 96/14566 | 5/1996 |

* cited by examiner

*Primary Examiner*—Frank G. Font
*Assistant Examiner*—Sang H. Nguyen
(74) *Attorney, Agent, or Firm*—Volentine Francos, PLLC

(57) ABSTRACT

A method and device detect for the presence of defects, namely micro-scratches, in the surface of a wafer. Light is projected onto a medium at the surface of the wafer, at an angle at which light is not reflected by another layer that may be located under the medium. Light reflected by the surface of the wafer is converted into an electrical signal but any light scattered by the surface is excluded as much as possible from contributing to the formation of the signal. The electric signal corresponds to the intensity of the light reflected from the surface of the wafer. As the light is scanned across the wafer, the values of the electric signal are compared to yield a determination of whether defects are present in the medium. Because the light projected onto the surface of the wafer will be scattered by defects such as micro-scratches, the wafer can be successfully monitored for the existence of such micro-scratches. In particular, defects including micro-scratches formed in the medium can be detected regardless of the structure underlying the medium, such as a pattern layer.

4 Claims, 14 Drawing Sheets

METHOD OF AND DEVICE FOR DETECTING MICRO-SCRATCHES

CROSS REFERENCE TO RELATED APPLICATIONS

This is a divisional application of application Ser. No. 09/584,671, filed Jun. 1, 2000, which is hereby incorporated by reference in its entirety for all purposes.

BACKGROUND OF THE INVENTION

1. Field of the Invention

The present invention relates to a method of and to a device for detecting micro-scratches in a semiconductor wafer.

2. Description of the Related Art

In the manufacturing of semiconductor devices, chemical and mechanical planarization (CMP) is a global planarization (GP) process for polishing a wafer. In CMP, slurry is sprayed onto the wafer and the wafer is polished with the slurry using a polyurethane polishing pad. The slurry contains silica particles as an abrasive. Some of the silica particles have a diameter equal to or greater than 1 $\mu$m which greatly exceeds the average diameter of the silica particles making up the slurry. These large particles apply abnormal stresses to the wafer during polishing. Portions of the wafer to which abnormal stresses have been applied fracture to relieve the stress.

FIG. 1 is a magnified view of the surface of a scratched wafer, and FIG. 2 is a cross-sectional view of a scratched wafer.

As shown in FIG. 1, scratches shaped like human eyebrows are formed on a wafer by CMP. Generally, the width of such a scratch is 0.3 to 3.0 $\mu$m, the length thereof is 3 to 30 $\mu$m, and the depth thereof is about 200 to 2000 Å. Although micro-scratches on the surface of a wafer can not be easily observed after CMP, the micro-scratches are enlarged during etching because weaker portions of the wafer bearing the micro-scratches are etched more heavily than the other portions of the wafer. The micro-scratches once so enlarged can be easily observed.

It is known that even when large silica particles account for only about 0.1% of the slurry, a large number of scratches are produced. However, it is difficult to remove large silica particles from the slurry, and to measure the amount of the large silica particles.

Moreover, the polyurethane polishing pad is porous and also produces micro-scratches in the wafer. The surface of the polishing pad has a roughness of several $\mu$m in virtue of the pores existing at the surface of the polishing pad. Slurry collects in the pores open at the surface of the polishing pad. When polishing is started in this state, stress is applied to the polishing pad by the wafer. Thus, polishing is performed by part of the slurry that exists at the surface of the wafer and in the pores of the pad. During this process, large silica particles lodged in the pores of the polishing pad scratch the surface of the wafer.

Conventional methods for detecting scratches include a method of irradiating monochrome laser light onto a surface and detecting the sizes of scratches in the surface using the light scattered from the surface, a method using scattered light from dies and detecting the scratches by a die-to-die signal processing, and a method of obtaining a highly-magnified video image of a surface using white light as an optical source and detecting scratches in the surface using the signal difference between pixels of the video camera.

However, these conventional methods of detecting scratches or defects in a wafer cannot effectively detect micro-scratches since they do not possess a high enough degree of resolution or an accurate enough image recognition ability.

SUMMARY OF THE INVENTION

An object of the present invention is to provide a method by which defects such as micro-scratches in a wafer can be effectively detected, and to provide a device for doing the same. That is, an object of the present invention is to provide a method of and a device for detecting micro-scratches, which method and device provide a high recognition rate of wafer defects and which allow the presence of such defects to be promptly confirmed.

To achieve this object, the present invention provides a method of detecting micro-scratches, in which the surface of a wafer is scanned with light from a light source while the light remains incident upon the surface of the wafer at a predetermined angle, the light reflected by normal portions of the surface ( i.e., at an angle of reflection substantially identical to that of the angle of incidence) propagates to an optical detector, the light received by the optical detector is used to generate an electrical signal indicative of the intensity of the received light, values are assigned to the electric signal in correspondence with the intensity of the light represented thereby, and whether defects are formed at the surface of the wafer is determined by comparing the values assigned to the electrical signal to each other.

Preferably, the light reflected by the surface of the wafer is divided into s polarized light and p polarized light, and the electrical signal is obtained from the s polarized light and/or the p polarized light.

Furthermore, the method also preferably takes measures to lengthen the optical path along which light travels from the light source to the wafer and/or from the surface of the wafer to the optical detector, thereby allowing flexibility in design for providing an appropriate angle of incidence. Such measures include bending the light by reflection and/or refraction. Moreover, the method includes a step of adjustably controlling the angle of incidence.

It is also preferable that the measures taken to lengthen the optical path cause the light to be confined in a first space located between the light source and the wafer and in a second discrete space located between the surface of the wafer and the optical detector. In this case, the light is reflected several times in each of the discrete spaces.

The present invention also provides a device for detecting micro-scratches, including a wafer stage, an optical system which produces light directed onto the wafer, a scanning mechanism which moves the optical system and the stage relative to one another so that the light is scanned across the wafer, a signal detection system which receives the light reflected by the wafer and converts the reflected light into an electrical signal, and a signal analysis system which analyzes the electrical signal. The optical system includes a light source, and light produced by the light source is directed onto the wafer surface at a predetermined angle. The signal detection system which receives the reflected light generates an electrical signal indicative of the intensity thereof. The signal analysis system compares values of the electrical signal with reference to different portions of the wafer surface which are scanned by the light, and this comparison yields a determination of whether defects have been formed in the surface of the wafer.

Furthermore, the signal detection system may include a polarization element which divides the reflected light into s polarized light and p polarized light, and polarized light detectors for converting the polarized light into electrical signals. The signal analysis system preferably determines from these electrical signals whether micro-scratches are present in the surface of the wafer.

A grazing optical system for lengthening the optical path is provided between the optical system and the wafer and between the wafer and the signal detection system. The grazing optical system has first and second mirrors disposed parallel to each other and perpendicular to the planar surface of the wafer. The light source projects light onto one of the mirrors at a predetermined angle of incidence, and light is reflected from one of the mirrors onto the surface of the wafer.

A third mirror may be provided for reflecting light from the light source onto one of the first and second mirrors. The inclination of the reflective surface of the third mirror is adjustable so that the third mirror controls the direction of the incident light.

Still further, a fourth mirror may be interposed between the first and second mirrors. In this case, the fourth and first mirrors coact and the second and fourth mirrors coact to confine the light to first and second discrete spaces, respectively. That is, the path along which light travels from the light source to the wafer, and the path along which the light reflected by the wafer travels to the signal detection system are separate from one another.

BRIEF DESCRIPTION OF THE DRAWINGS

The above and other objects, features and advantages of the present invention will become more apparent by referring to the following detailed description of preferred embodiments thereof made with reference to the attached drawings, of which.

DETAILED DESCRIPTION OF THE PREFERRED EMBODIMENTS

Figure 1:
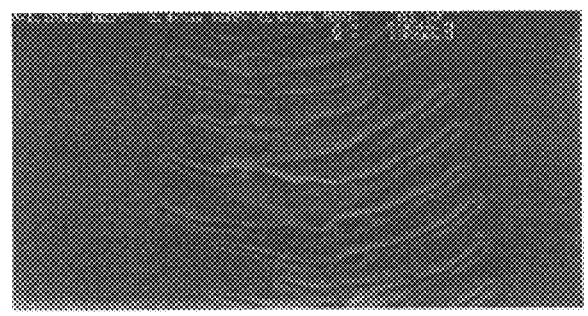
FIG. 1 is a magnified view of the surface of a scratched wafer.
Figure 2:
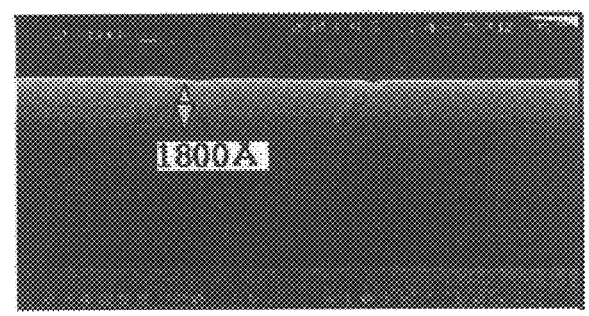
FIG. 2 is a magnified sectional view of a scratched wafer.
Figure 3:
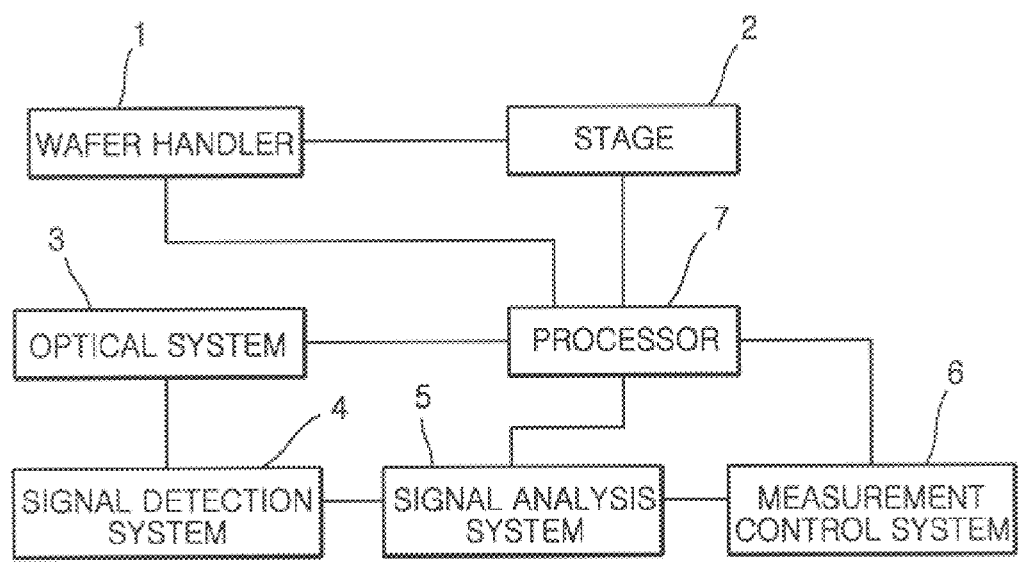
FIG. 3 is a block diagram of a first embodiment of a device for detecting micro-scratches according to the present invention.

Referring to FIG. 3, a wafer handler 1 can transfer a wafer to be examined to and from a stage 2. An optical system 3 irradiates light onto the wafer supported by the stage 2. A signal detection system 4 detects the light which is reflected by the wafer and converts the reflected light into an electrical signal. A signal analysis system 5 determines whether the surface of the wafer has been scratched using the electrical signal generated by the signal detection system 4. A measurement control system 6 controls items which are associated with several types of measurements including the optical system 3. A processor 7 such as a computer controls. all of the above-mentioned systems.

The optical system 3 includes a light source which generates light ranging in wavelength from deep ultraviolet (DUV) to infrared. The signal detection system 4 and the signal analysis system 8 are configured according to the wavelength of light produced by the light source.

Figure 4:
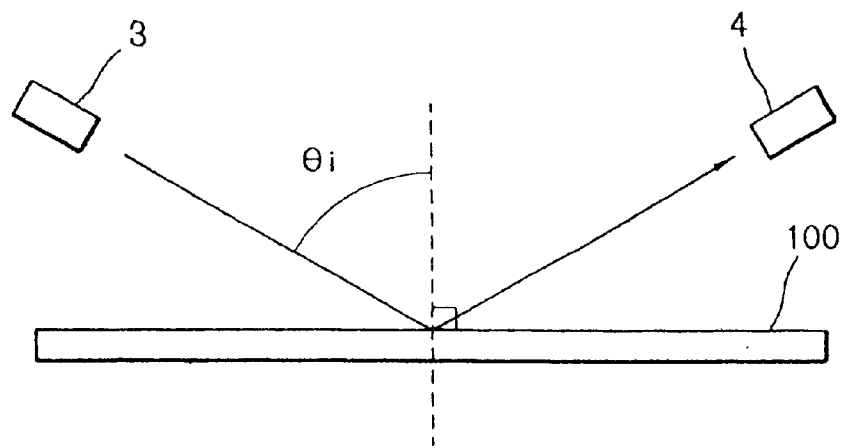
FIG. 4 is a schematic diagram illustrating the relationship between the optical system and the signal detection system of the first embodiment of the device for detecting micro-scratches according to the present invention.

Referring now to FIG. 4, white light, monochrome light or light of a predetermined color radiating from the light source of the optical system 3 is incident upon the surface of the wafer 100 to be examined, at a predetermined incidence angle ($\theta_i$). Light reflected by the wafer 100 is incident upon the signal detection system 4.

The signal detection system 4 is provided at a location where only light reflected by the surface of wafer 100 would propagate, i.e., the signal detection system 4 will receive only a minimum amount of scattered light. In fact, preferably none of any light scattered from the surface of the wafer falls upon the signal detection system 4. The signal detection system 4 includes an optical detector for converting incident light into an electrical signal.

The incidence angle ($\theta_i$) is within a range where most of the light from the optical system 3 will be reflected, and is selected based on the refractive index (n) of a target material layer (medium) at the surface of a wafer under examination. Here, the incidence angle ($\theta_i$) is greater than 0 and less than 90 degrees.

Figure 5:
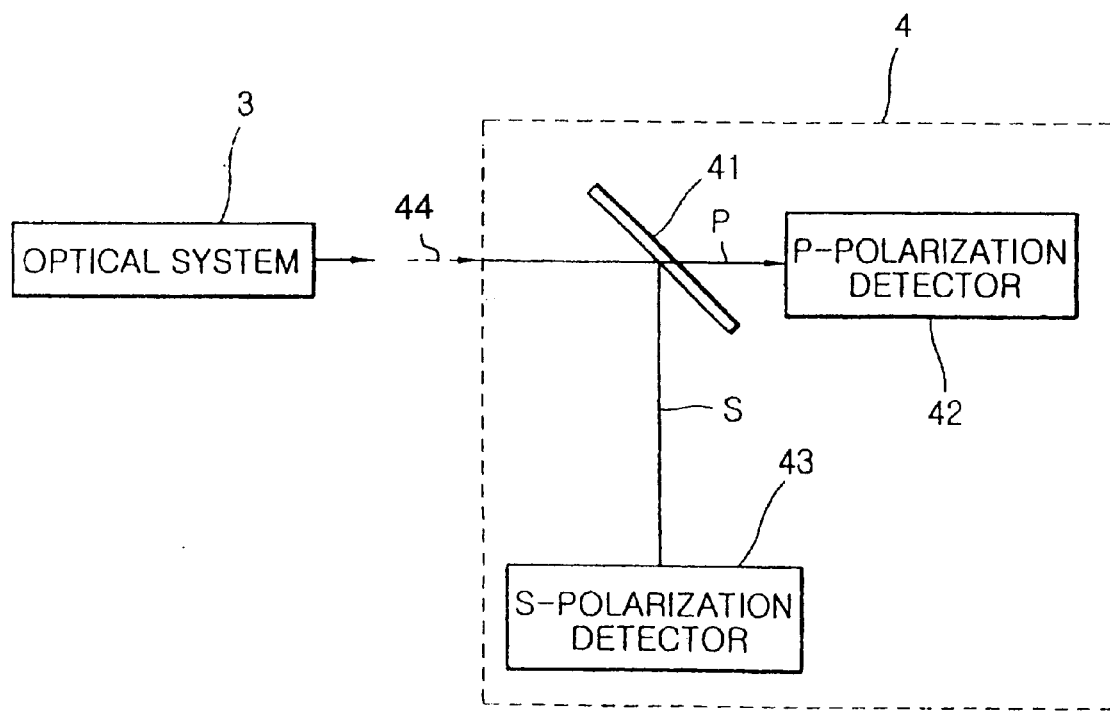
FIG. 5 is a block diagram of an optical detection system of a second embodiment of a device for detecting micro-scratches according to the present invention.

FIG. 5 illustrates an optical detection system 4 of a second embodiment of the present invention. Referring to FIG. 5, light which is output from the optical system 3 and reflected by the surface of a wafer is incident upon a beam splitter 41 of the optical detection system 4. The beam splitter 41 is inclined at a predetermined angle with respect to an optical axis 44. Among the incident light, P polarized light is incident upon a P polarization detector 42 via the beam splitter 41, and S polarized light is reflected by the beam splitter 41 so as to fall upon an S polarization detector 43. Here, a photo array detector or a CCD camera can be used as the P polarization detector 42 and the S polarization detector 43.

An electrical signal obtained by the signal detection system 4 is supplied to the signal analysis system 5. The signal analysis system 5 determines whether micro-scratches have been produced in specific areas of a wafer surface, using the received electrical signal.

Simulation 1

This simulation studies the variation in reflectivity with respect to the variation in incidence angle of light upon a medium layer at a wafer surface under the conditions below. In this simulation, the incidence angle ($\theta_i$) varies between 0 and 90 degrees, the light has a wavelength of 632.8 nm, and silicon oxide having a refractive index (n) of 1.462 was used as the medium layer formed at the wafer surface. Also, the signal detection system of the embodiment of FIG. 5 was used, whereby the reflected light was split into p polarized light waves and s polarized light waves.

The reflectivity (Rs) of the s polarized light waves and the reflectivity (Rp) of the p polarized light waves with respect to the medium layer are defined by Equations 1 and 2 according to Snell's law:

$$Rs=\pm\{((n\times\cos\theta n)-(1\times\cos\theta i))\div((n\times\cos\theta n)+(1\times\cos\theta i))\} \quad (1)$$

$$Rp=\pm\{((n\div\cos\theta n)-(1\div\cos\theta i))\div((n\div\cos\theta n)+(1\div\cos\theta i))\} \quad (2)$$

wherein θn denotes the angle of refraction of light within a medium.

Figure 6:
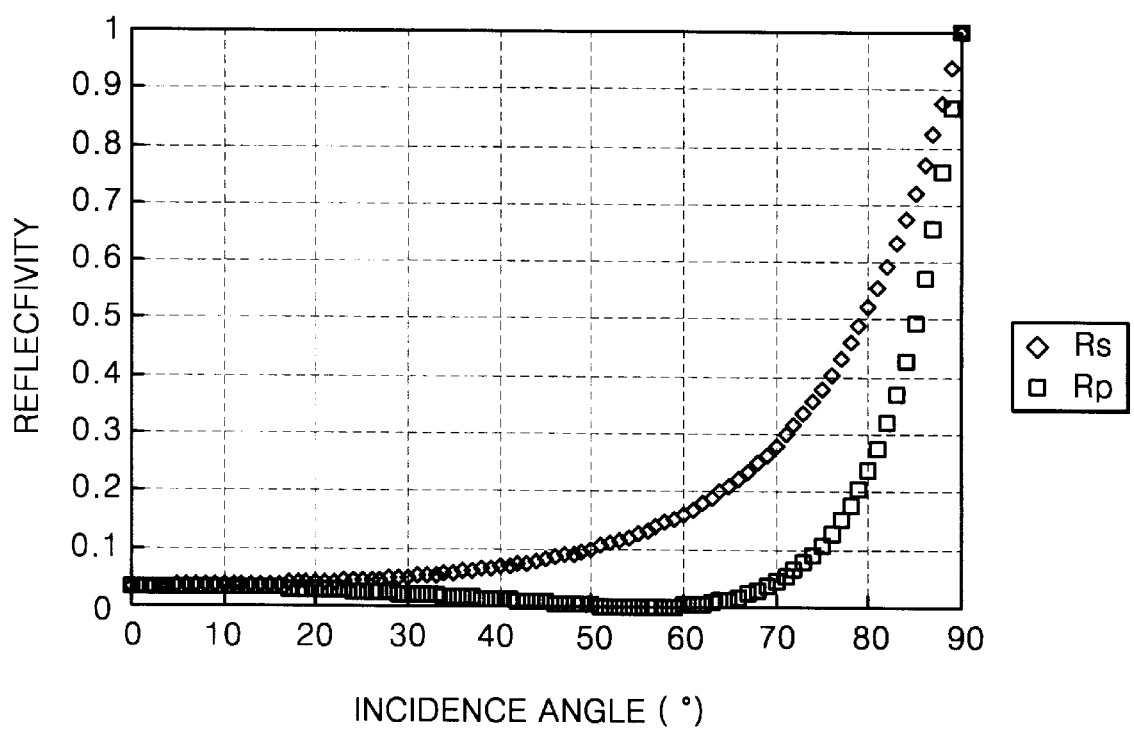
FIG. 6 is a graph showing variations in the reflectivity (Rs) of s polarized light and the reflectivity (Rp) of p polarized light in Simulation 1 according to the present invention.

The simulation performed under the above-described conditions resulted in variations in the reflectivity (Rs) of the s polarized light and the reflectivity (Rp) of the p polarized light as shown in FIG. 6.

Referring to FIG. 6, the reflectivity (Rs) of s polarized light increases with an increase in incidence angle (θi), and sharply increases particularly when the incidence angle (θi) exceeds 70 degrees. Also, the reflectivity (Rp) of p polarized light decreases up to where the incidence angle (θi) is 65 degrees, and then sharply increases after this point. Here, the angle at which the reflectivity (Rp) of p polarized light is minimum is Brewster's angle at which most of incident light passes through the medium.

According to these results, when the incidence angle (θi) is greater than a predetermined value, particularly, when the p polarized light is incident at an angle which is greater than Brewster's angle, particularly, at least 85 degrees, light incident upon a medium layer is mostly reflected. Therefore, such light is particularly useful for detecting defects such as micro-scratches in the surface of the medium layer. That is, if the angle of incidence is kept at least 85 degrees, defects can be detected based on the amount of light incident upon the signal detection system 4. More specifically, if the light is reflected by a normal portion of the surface of the target medium layer, nearly all of the reflected light falls on the signal detection system 4, but if the light is scattered by defects such as micro-scratches in the layer, only part of the scattered light falls on the signal detection system 4.

Simulation 2

This simulation examines the effect that an underlying layer pattern has upon the variation in reflectivity with respect to the variation in incidence angle (θi) when an underlying layer pattern exists under the target medium layer on the surface of a wafer. Using these results, this simulation also serves to examine the effect that the underlying layer pattern has on the detection of micro-scratches in the surface of the target medium layer.

In this simulation, the optical incidence angle (θi) ranges from 0 to 90 degrees, the incident light has a wavelength of 632.8 nm, and silicon oxide having a thickness of 10000 to 13000 Å and a refractive index (n) of 1.462 was used as the medium layer formed at the wafer surface. The pattern layer under the medium layer had a thickness of 35000 Å, and the refractive indices of the pattern layer and a substrate were 1.3402 and 3.8806, respectively.

Figure 7:
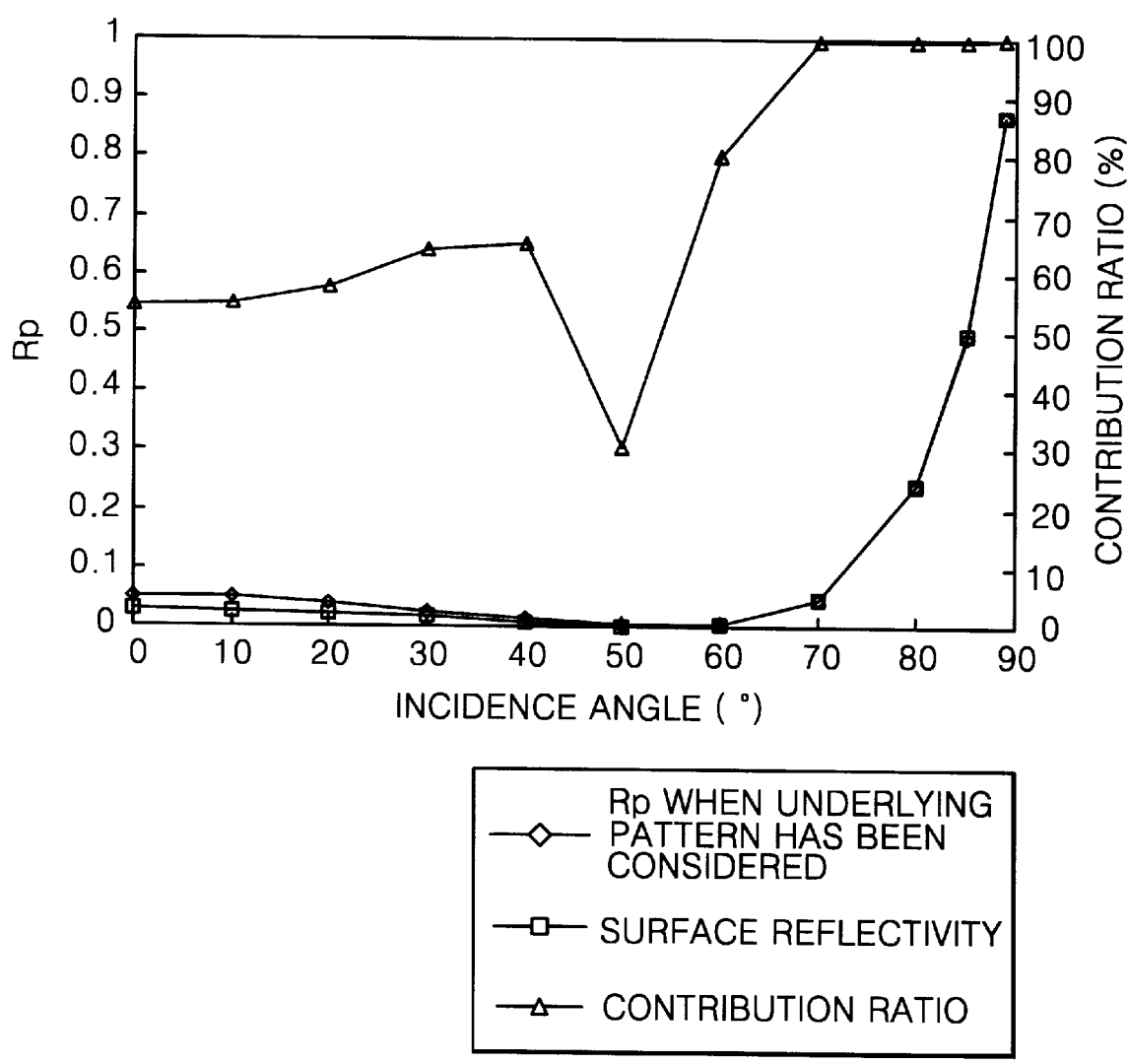
FIG. 7 is a graph showing variations in the reflectivity (Rp) of the p polarized light wave in Simulation 2 according to the present invention.
Figure 8:
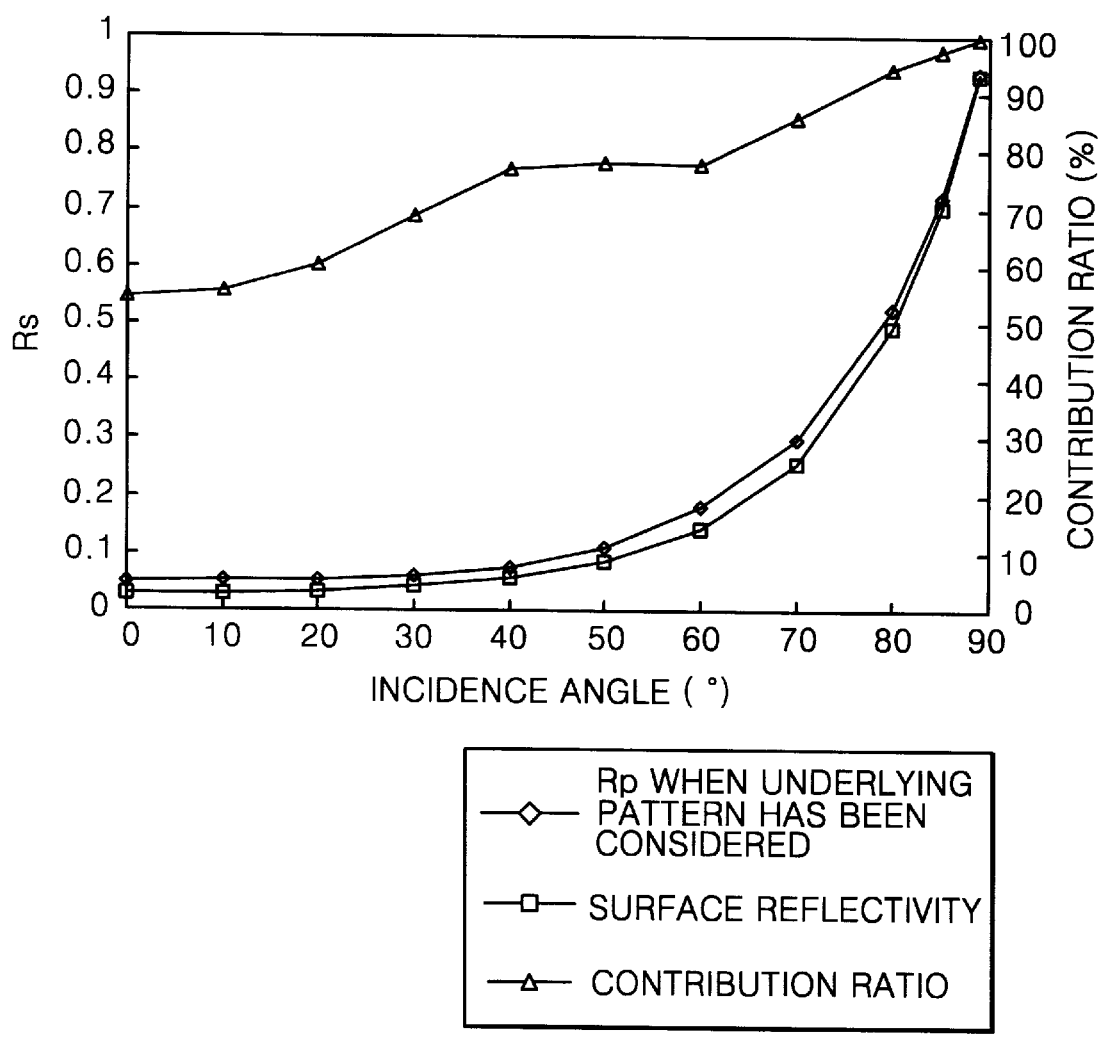
FIG. 8 is a graph showing variations in the reflectivity (Rs) of the s polarized light in Simulation 2 according to the present invention.
Figure 9:
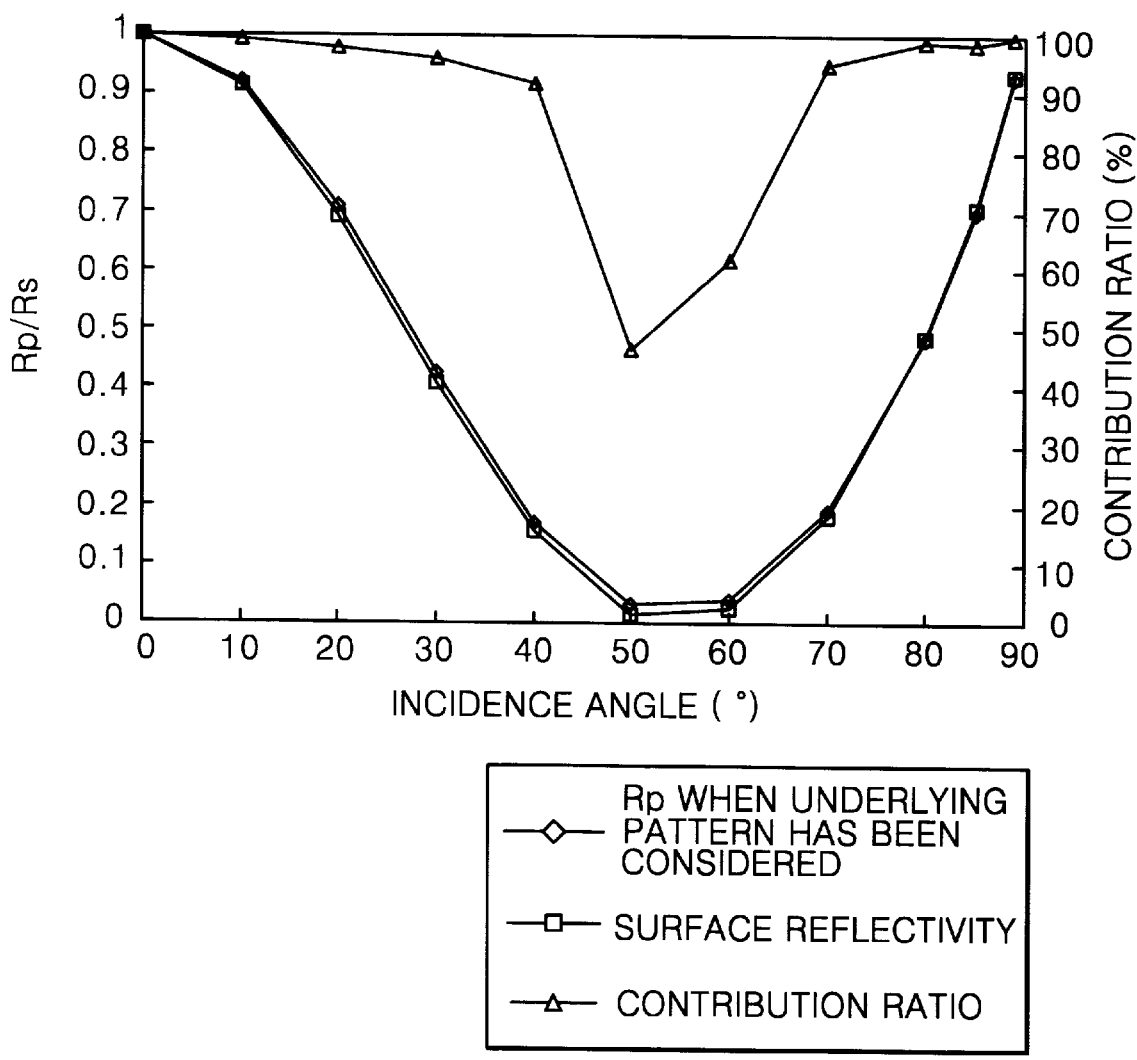
FIG. 9 is a graph showing variations in the ratio of the reflectivity (Rp) of the p polarized light to the reflectivity (Rs) of the s polarized light in a state where an underlying pattern layer has been considered, in Simulation 2 according to the present invention.

Simulation 2 under the above-described conditions produced results such as those shown in FIGS. 7 through 9. FIG. 7 shows variations in the reflectivity (Rp) of the p polarized light, and FIG. 8 shows variations in the reflectivity (Rs) of the s polarized light. In FIGS. 7 and 8, the term contribution ratio denotes a ratio of the reflectivity of the medium layer to the reflectivity when the underlying pattern layer has been considered. A large contribution ratio indicates that the underlying pattern layer exerts only a small influence on the reflectivity of the medium layer.

As shown in FIG. 7, the reflectivity of p polarized light when the underlying pattern has been considered decreases when the incidence angle is between 0 and 50 degrees, and does not appear when the incidence angle is 50 degrees or more. The surface reflectivity of the medium layer gradually decreases as the incidence angle increases from 0 to 50 degrees, but gradually increases for incidence angles of 50 degrees or more, and sharply increases from 80 degrees. Also, the contribution ratio is greatly lowered around the Brewster's angle and reaches nearly 100% at an incidence angle of 70 degrees or more.

As shown in FIG. 8, the contribution ratio increases with an increase in the incidence angle (θi), and is 90% or more when the incidence angle is 80 degrees or more.

FIG. 9 shows variations in the ratio of the reflectivity (Rp) of the p polarized light to the reflectivity (Rs) of the s polarized light, in a state where an underlying pattern layer has been considered. As shown in FIG. 9, the reflectivity ratio (Rp/Rs) decreases together with the contribution ratio as the incidence angle (θi) increases, and sharply increases as the incidence angle increases from 50 degrees.

According to Simulation 2 as described above, the contribution ratio of the reflectivity (Rp) of the p polarized light is more stable than the contribution ratio of the reflectivity (Rs) of the s polarized light and that of the ratio (Rp/Rs) of the reflectivity of the p polarized light to the reflectivity of the s polarized light. The contribution ratio of the reflectivity (Rp) of the p polarized light is high over a wide range. This shows that p polarized light is advantageous in detecting micro-scratches in a medium layer.

Simulation 3

Simulation 3 examines the signal-to-noise ratio (SNR) of the surface reflectivity of a medium layer with respect to the change in the pattern of an underlying pattern layer and the variation in incidence angle (θi) when the lower pattern layer is provided under the medium layer on a wafer surface.

In Simulation 3, the optical incidence angle (θi) ranges from 0 to 90 degrees, the light has a wavelength of 632.8 nm, and silicon oxide having a thickness of 1000 to 13000 Å and a refractive index (n) of 1.462 was used as the medium layer which is formed on the wafer surface. The pattern layer under the medium layer has a thickness of 35000 Å, and the refractive indices of the pattern layer and a substrate were 1.3402 and 3.8806, respectively. The reflectivity was measured for different thicknesses of the medium layer of between 10000 Å to 13000 Å increased by increments of 30 Å. Here, the SNR denotes the ratio of the mean of reflectivity to the variation in reflectivity with respect to the variation in the thickness of the medium layer.

Figure 10:
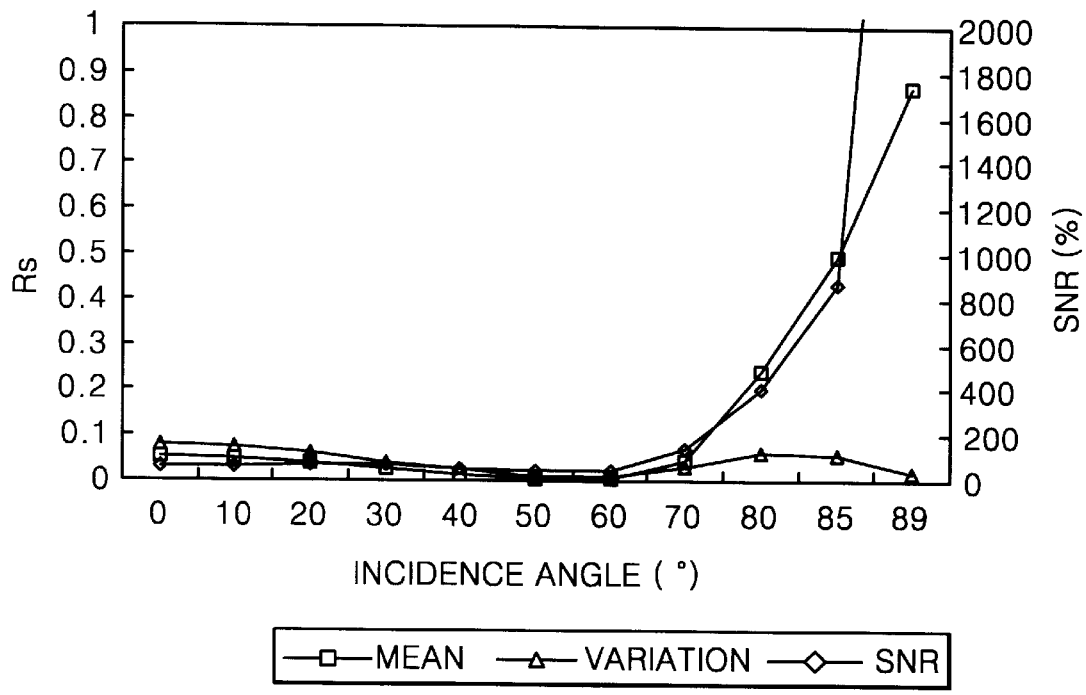
FIG. 10 is a graph showing variations in signal-to-noise ratio (SNR) and variations in the reflectivity (Rp) of p polarized light with respect to the incidence angle, in Simulation 3 according to the present invention.

Referring to FIG. 10, the variation in the reflectivity of p polarized light becomes smaller than the mean of the reflectivity from when the incidence angle is 70 degrees. Thus, the SNR sharply increases.

Figure 11:
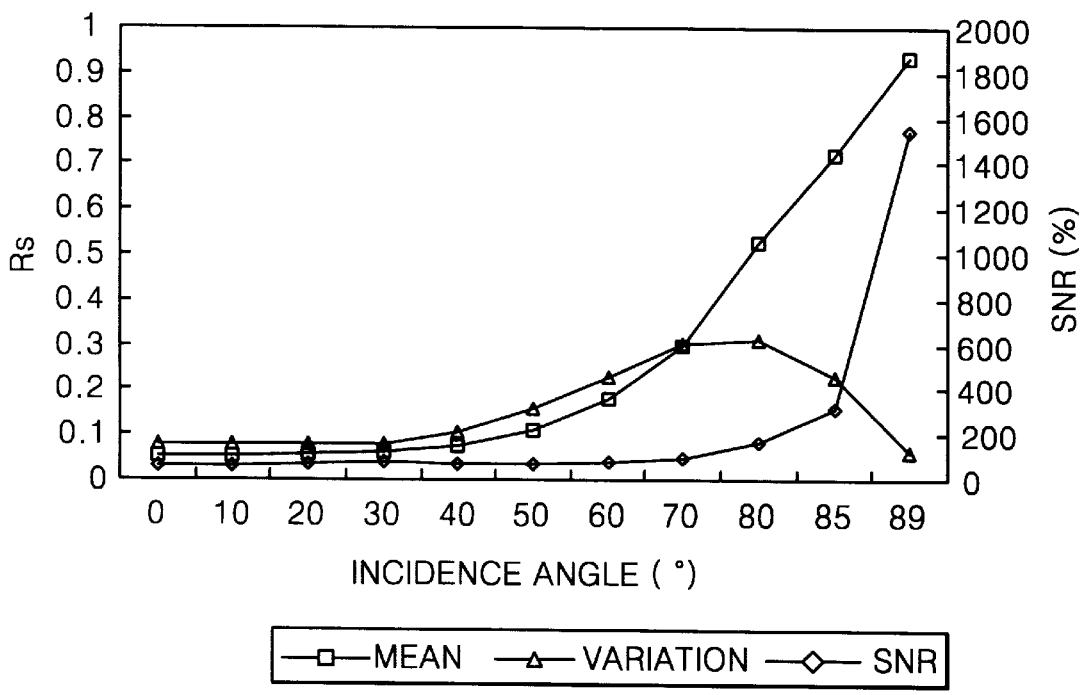
FIG. 11 is a graph showing variations in SNR and variations in the reflectivity (Rs) of s polarized light with respect to the incidence angle, in Simulation 3 according to the present invention.

Referring to FIG. 11, the SNR increases as the variations in the reflectivity of s polarized light and the incidence angle increase. Particularly, the SNR is 300% or more from when the incidence angle is 85 degrees or greater.

Figure 12:
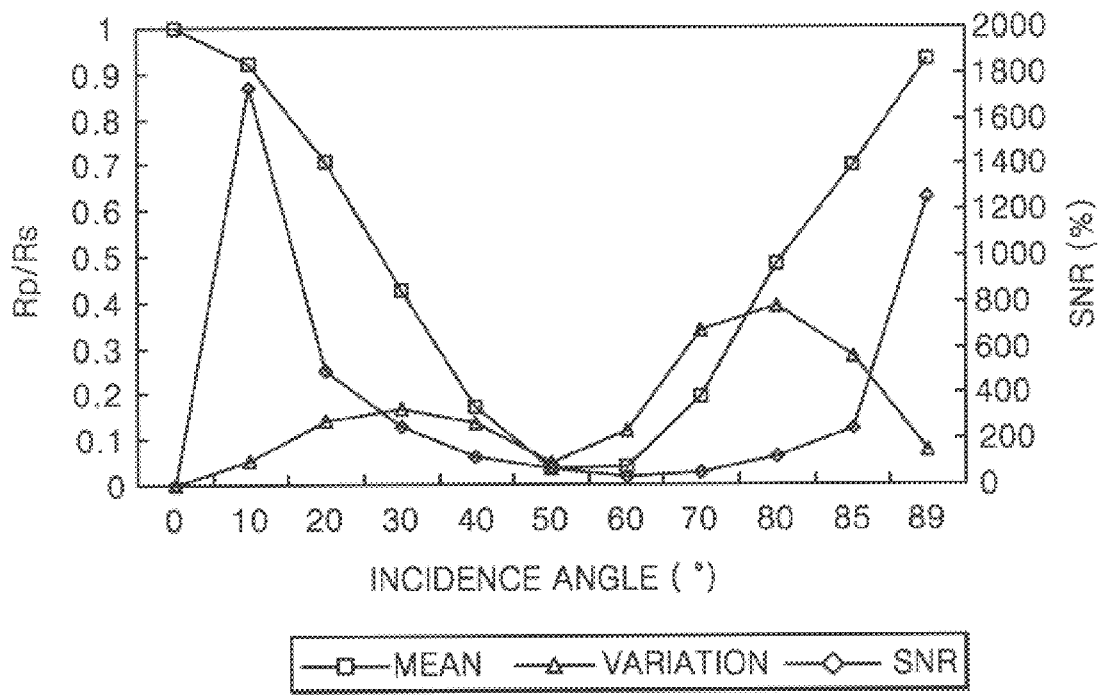
FIG. 12 is a graph showing variations in SNR and variations in the ratio of the reflectivity (Rp) of p polarized light to the reflectivity (Rs) of s polarized light with respect to the incidence angle, in Simulation 3 according to the present invention.

Referring to FIG. 12, with an increase in the incidence angle to 50 or 60 degrees or greater, a variation in the ratio of the reflectivity (Rp) of p polarized light waves to the reflectivity (Rs) of s polarized light waves becomes much smaller than the mean of the reflectivity. Thus, the SNR sharply decreases.

According to Simulation 3 as described above, the SNR of the reflectivity (Rp) of the p polarized light is more stable than the SNR of the reflectivity (Rs) of the s polarized light and the SNR of the ratio (Rp/Rs) of the reflectivity of the p polarized light to the reflectivity of the s polarized light. The SNR of the reflectivity (Rp) of the p polarized light is high over a wide range. This shows that p polarized light can be useful in detecting micro-scratches in a medium layer.

Simulation 4

Figure 13:
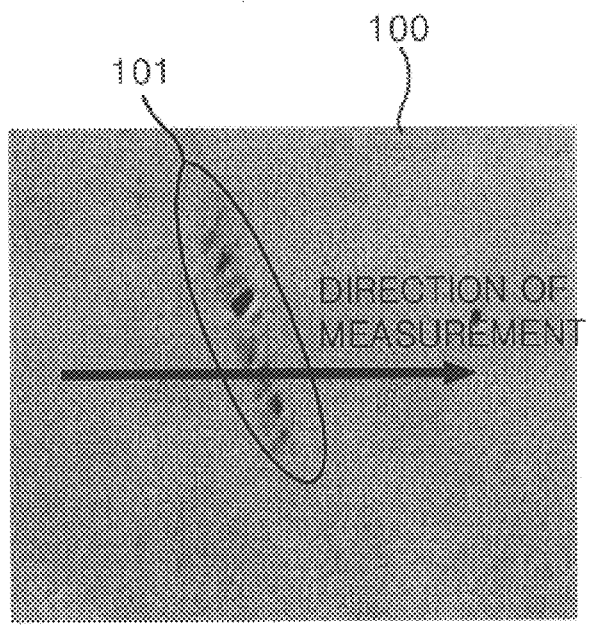
FIG. 13 is a schematic diagram showing the direction in which a wafer surface in which micro-scratches are formed is scanned, in Simulation 4 according to the present invention.

Simulation 4 examines a variation in the amount of light reflected at micro-scratches in a medium layer formed on the surface of a wafer, with a variation in incidence angle. In Simulation 4, the incidence angle ranges from 45.9 to 64.2 degrees, the wavelength of the incident light is 632.8 nm, and the incident light was scanned over a distance of 5 μm in a direction of crossing a micro-scratch 101 formed in a medium layer of a wafer 100 as shown in FIG. 13. The size of a light spot was set to be 5×10 μm.

By using signal analysis, a corrected value was obtained by amplifying a signal using Equation 3 defined with reflectivity ratios Data1 and Data2 which were obtained from two adjacent scanned portions:

$$\text{corrected value} = ((|Data1 - Data2 \times |10)^{\wedge}2)/10 \quad (3)$$

wherein reflectivity ratios Data1 and Data2 denote ratios of the reflectivity of p polarized light to the reflectivity of s polarized light.

Figure 14:
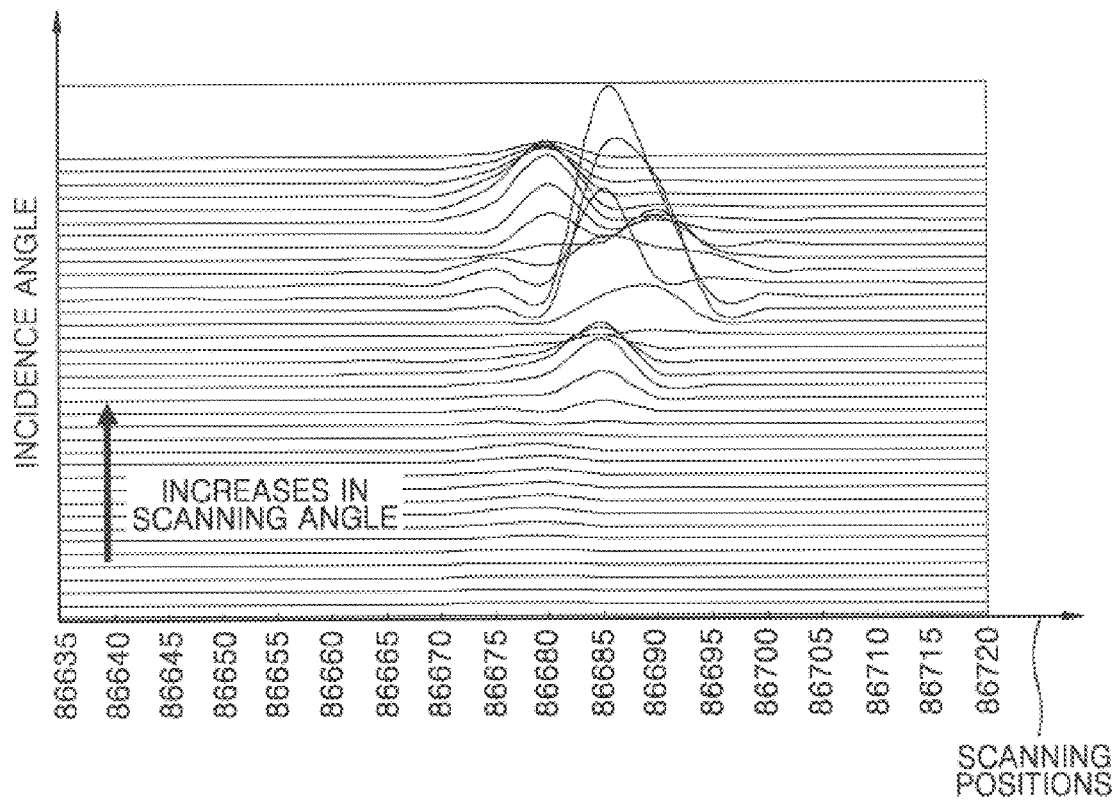
FIG. 14 is a graph showing variations in the ratio of the reflectivity (Rp) of the p polarized light to the reflectivity (Rs) of the s polarized light with respect to variations in incidence angle, in Simulation 4 according to the present invention.

Referring to FIG. 14, with an increase in incidence angle, a change in the ratio of the reflectivity of p polarized light to the reflectivity of s polarized light starts occurring at portions damaged by micro-scratches, and the magnitude of the change gradually increases.

It can be seen from FIG. 14 that the ratio (Rp/Rs) of reflection by micro-scratches in a medium layer of a wafer greatly varies with an increase in incidence angle, and the sensitivity of detection of micro-scratches greatly increases accordingly.

Simulation 5

Figure 15:
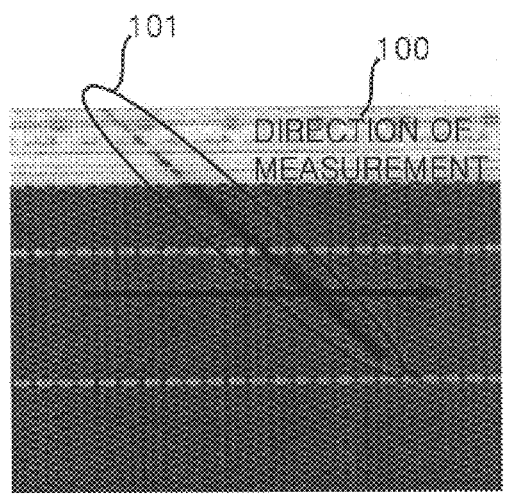
FIG. 15 is a schematic diagram showing the direction in which a wafer surface in which micro-scratches are formed is scanned, in Simulation 5 according to the present invention.

Simulation 5 examines an actually-measured value when areas damaged by micro-scratches are scanned using a micro-scratch detection device according to the present invention. In Simulation 5, the incidence angle was fixed at 65.07 degrees, the wavelength of the incident light was 632.8 nm, and the scanning intervals in the directions of the horizontal axis and the vertical axis were set to be 5 μm and 10 μm, respectively. The incident light was scanned across a micro-scratch 101 formed in a medium layer of a wafer 100, as shown in FIG. 15. The size of the light spot with respect to the medium layer was set to be 5×10 μm.

Here, the ratio (Rp/Rs) of the reflectivity of p polarized light to the reflectivity of s polarized light was measured. By using signal analysis, a corrected value was obtained by amplifying a signal using Equation 4 which is defined with reflectivity ratios Data1 and Data2 which were obtained from two adjacent scanned portions:

$$\text{corrected value} = ((|Data1 - Data2| \times 10)^{\wedge}10)/50 \quad (4)$$

Figure 16:
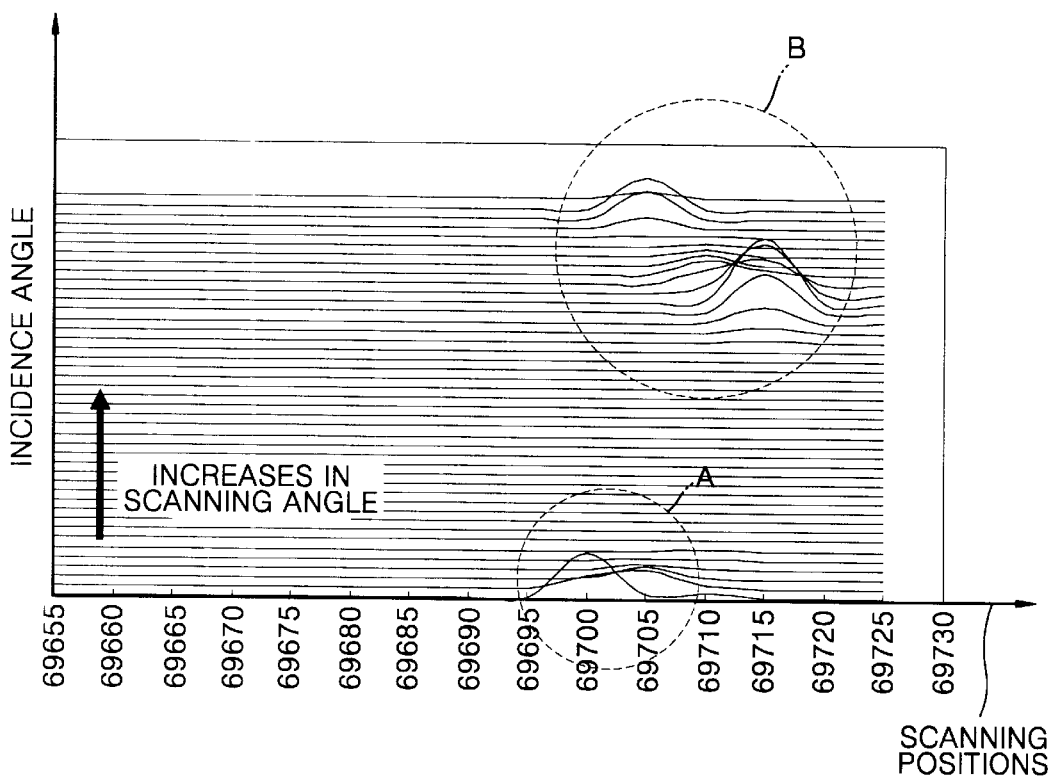
FIG. 16 is a graph showing variations in the ratio of the reflectivity (Rp) of the p polarized light to the reflectivity (Rs) of the s polarized light with respect to variations in incidence angle, in a state where a pattern layer under a medium layer has been considered, in Simulation 5 according to the present invention.

Referring to FIG. 16, with an increase in incidence angle, a change (B) in the ratio of the reflectivity of p polarized light to the reflectivity of s polarized light starts occurring at portions damaged by micro-scratches, and the magnitude of the change gradually increases. In FIG. 16, a radical change (A) in reflectivity ratio which appears at low incidence angles depends on a change in the thickness of a pattern layer under the medium layer.

Figure 17:
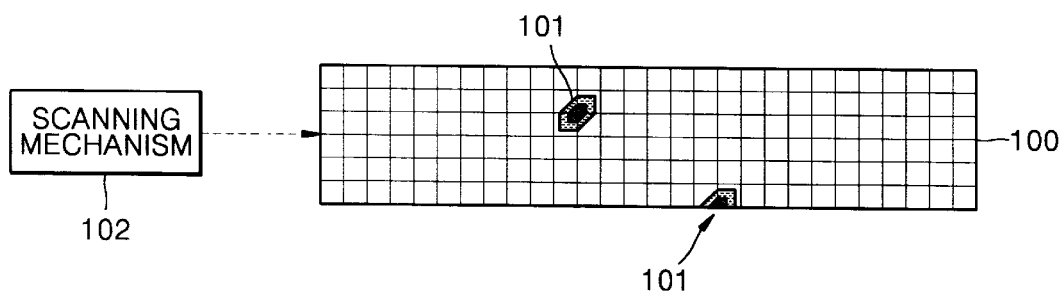
FIG. 17 is a diagram showing the results of scanning of a wafer surface in Simulation 5 according to the present invention.

FIG. 17 is an image of the result of scanning a wafer surface using the aforementioned device. Note, any appropriate mechanism 102 known, per se, can be used to move the wafer stage 2 and the optical system 3 relative to one another so that the light is scanned across the wafer. It can be seen from FIG. 17 that the ratio (Rp/Rs) of reflection by micro-scratches in a medium layer of a wafer greatly varies with an increase in incidence angle, and the sensitivity of detection of micro-scratches greatly increases accordingly.

That is, the present invention can detect the presence of micro-scratches in a wafer surface by maintaining an appropriate optical incidence angle with respect to the wafer surface.

As described above, the reflected light is divided into s polarized light and p polarized light, and a signal was generated based on the polarized light. According to the results of simulations, the p polarized light was shown to be more useful in indicating the presence of micro-scratches. However, as described above, when both s polarized light and p polarized light was kept at an incidence angle greater than a predetermined incidence angle, micro-scratches in a medium layer were capable of being observed without interference of reflected light from a pattern layer under the medium layer. Hence, although p polarized light is more appropriate for monitoring for micro-scratches in a wafer surface, s polarized light can also be used therefor. Moreover, micro-scratches in the surface of a wafer can be undoubtedly detected by converting reflected light into electrical signals without polarizing the reflected light.

As described above, it was found that larger incidence angles yield better results in monitoring for the presence of micro-scratches. However, as is evident from FIG. 4, an optical structure for directly irradiating light onto a wafer 100 is limited in terms of how great of an incidence angle it can provide. That is, the optical system 3 must be positioned closer to the surface of the wafer 100 as the incidence angle increases. However, it is difficult to design an optical system which can be positioned very close to the wafer surface, i.e., the design freedom of peripheral devices is severely compromised by such a requirement. The present invention overcomes this problem by providing a structure which allows the optical system 3 to be located sufficiently far away from the wafer and yet irradiate the wafer with light at a sufficiently large optical angle of incidence.

Figure 18:
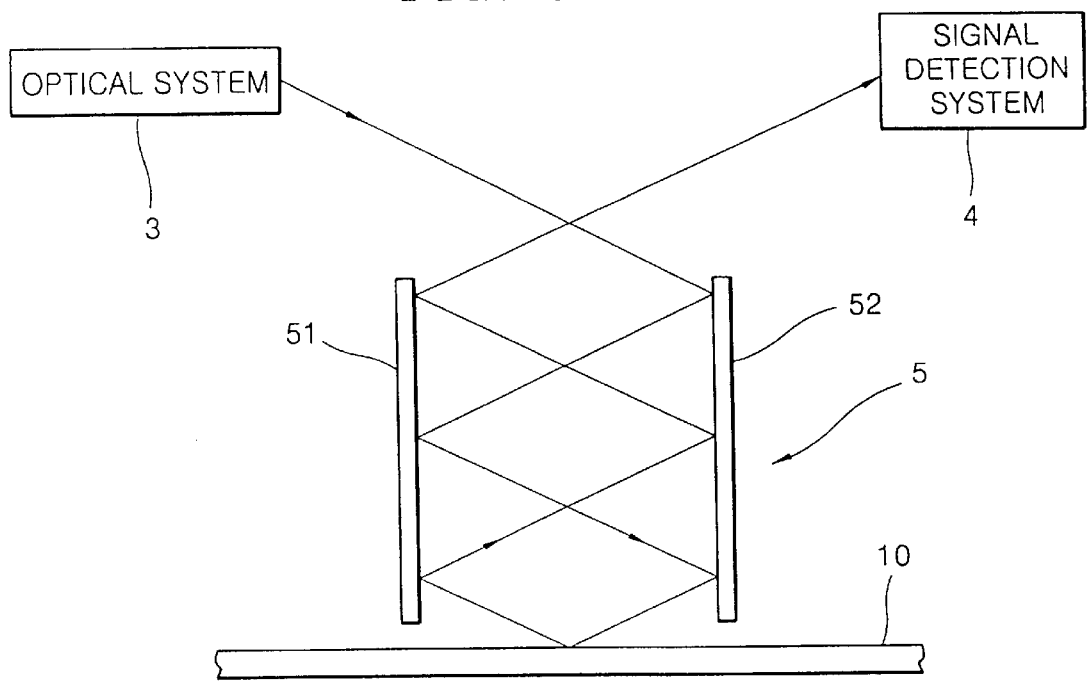
FIG. 18 is a schematic diagram of a third embodiment of a device for detecting micro-scratches according to the present invention.

FIG. 18 shows such a structure. In this embodiment, a grazing optical system 5 is provided between an optical system 3 and a signal detection system 4. With the optical system 3 positioned a significant distance away from the wafer 100, the grazing optical system 5 causes light from the optical system 3 to fall upon the surface of a wafer 100 at a large angle, and transmits light which has been reflected by the wafer 100 to the signal detection system 4.

More specifically, the grazing optical system 5 is disposed in an optical path between the optical system 3 and the signal detection system 4, and reflects light from the optical system 3 several times and directs the reflected light toward the surface of the wafer 100, and also reflects light reflected by the wafer 100 several times and directs the reflected light toward the signal detection system 4.

The grazing optical system 5 includes first and second mirrors 51 and 52 which are parallel to each other. Light from the optical system 3 is firstly reflected by the second mirror 52, and then proceeds toward the first mirror 51. Light reflected by the first mirror 51 proceeds back toward the second mirror 52. Light escapes from the first and second mirrors 51 and 52 through this repetition of reflection, and falls on the wafer 100. Light which has been reflected by the wafer 100 is again incident upon the first mirror 51 and reflected to the second mirror 52. The light from the wafer 100 is reflected several times between the first and second mirrors 51 and 52 as described above, and thus escapes from the first and second mirrors 51 and 52 and propagates toward the signal detection system 4.

Figure 19:
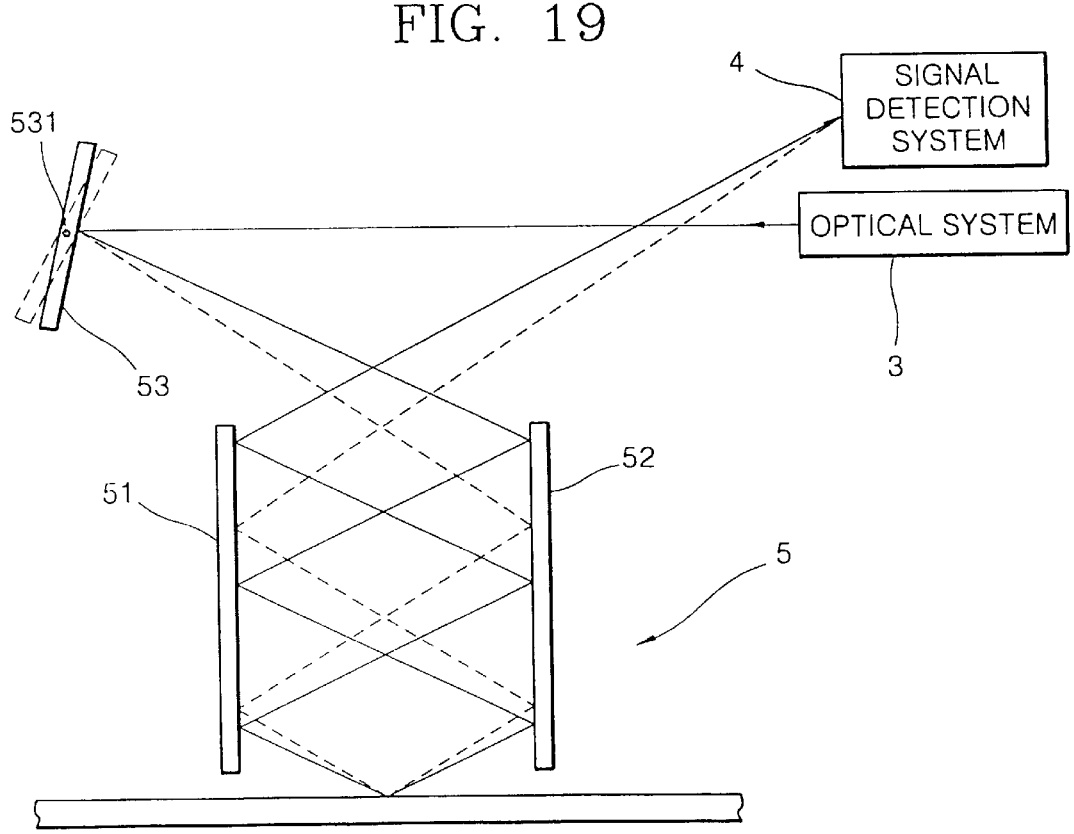
FIG. 19 is a schematic diagram of a fourth embodiment of a device for detecting micro-scratches according to the present invention.

FIG. 19 shows another embodiment of the present invention in which a grazing optical system 5 is provided between the optical system 3 and the signal detection system 4. In this embodiment, a third mirror 53 establishes the angle at which light from the optical system 3 falls on the wafer 100. Light from the optical system 3 falls upon the second mirror 52 via the third mirror 53. In such a structure, the optical system 3 and the signal detection system 4 may be placed on the same side. The third mirror 53 may be fixed at one place. Alternatively, the third mirror 53 may be rotatable about an axis 531 such that the angle of incidence can be varied. Accordingly, the angle of reflection can also vary. Also, the rotatable mount of the third mirror 53 allows the inclination of the third mirror 53 to be easily correctable.

Figure 20:
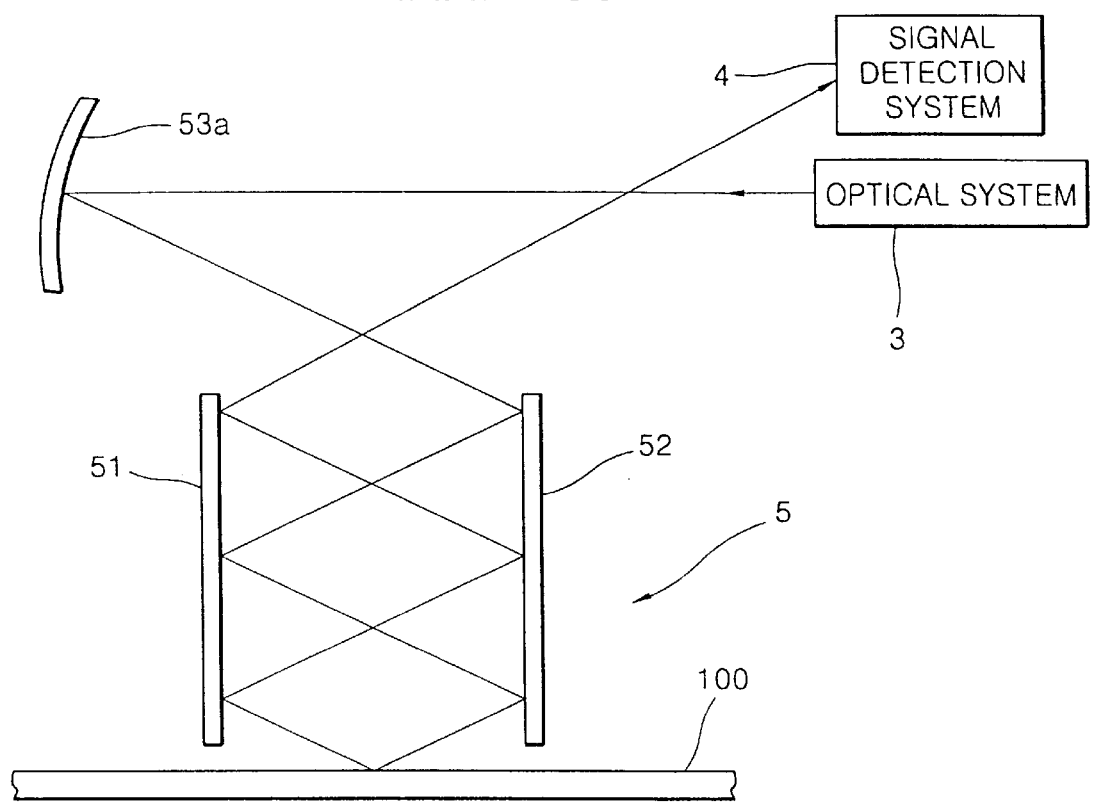
FIG. 20 is a schematic diagram of a fifth embodiment of a device for detecting micro-scratches according to the present invention.

FIG. 20 shows still another embodiment of the present invention in which a grazing optical system 5 is provided between the optical system 3 and the signal detection system 4. The grazing optical system 5 of FIG. 20 includes a third mirror 53a, e.g., a parabolic mirror, which focuses light onto the second mirror 52. The light focusing mirror 53a compensates for the divergence of light due to the extended optical distance between the optical system 3 and the surface of the wafer 100. Also, the third mirror 53a has a focusing power which corresponds to the optical distance, and accordingly can form a spot of a desired size on the surface of the wafer 100.

Figure 21:
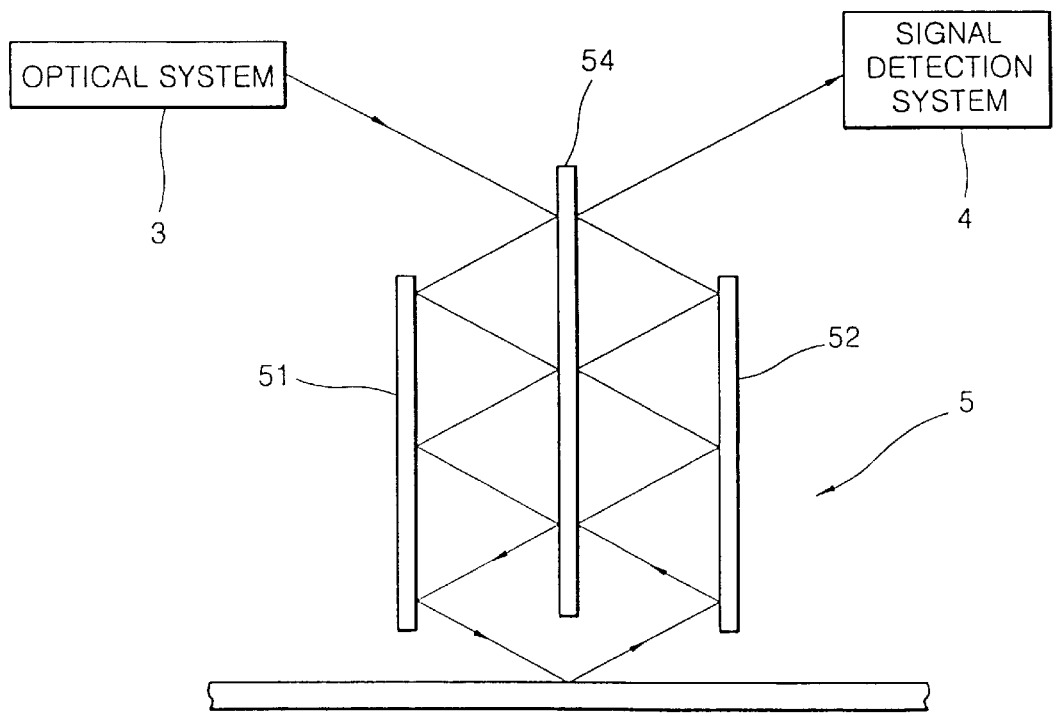
FIG. 21 is a schematic diagram of a sixth embodiment of a device for detecting micro-scratches according to the present invention.
Figure 22:
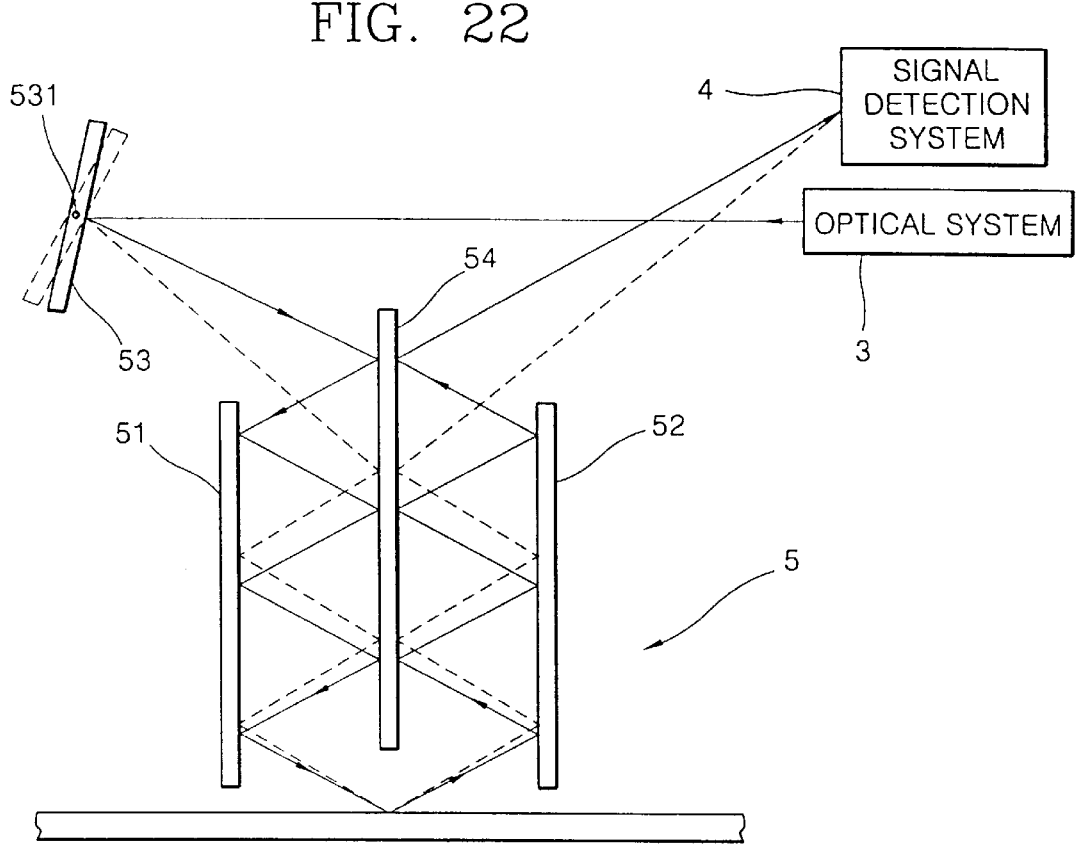
FIG. 22 is a schematic diagram of a seventh embodiment of a device for detecting micro-scratches according to the present invention.
Figure 23:
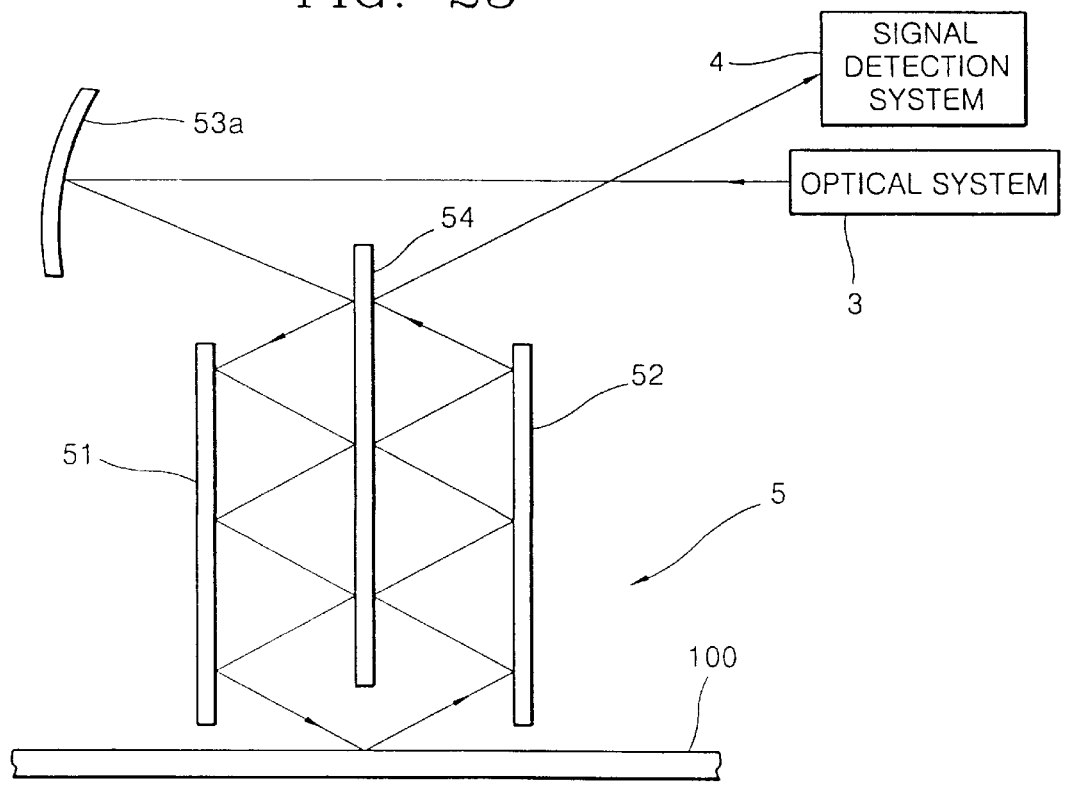
FIG. 23 is a schematic diagram, of an eighth embodiment of a device for detecting micro-scratches according to the present invention.

FIGS. 21, 22 and 23 show further embodiments, respectively, of a micro-scratch detection device according to the present invention, in which a grazing optical system 5 is provided between the optical system 3 and the signal detection system 4. The embodiments shown in FIGS. 21, 22 and 23 are similar to one another in that a fourth mirror 54 is provided between the first and second mirrors 51 and 52. The fourth mirror 54 separates and makes discrete from one another the path along which light travels toward the wafer 100 and the path along which light travels once reflected by the wafer. It can be seen from these figures that the first 51, second 52 and fourth 54 mirrors are positioned relative to each other such that the first 51 and fourth 54 mirrors coact to confine the light to a first space located between the optical system 3 and the wafer 100, and that the fourth 54 and second 52 mirrors coact to confine the light to a second space, discrete from the first space, located between the signal detection system 4 and the wafer 100.

The grazing optical system 5 shown in FIG. 21 is an application of the embodiment of the grazing optical system 5 shown in FIG. 18. Likewise, the grazing optical system 5 shown in FIG. 22 is an application of the embodiment of the grazing optical system 5 shown in FIG. 19. The grazing optical system 5 shown in FIG. 23 is obviously an application of the embodiment of the grazing optical system 5 shown in FIG. 20. Therefore, a detailed description of the operation of the detection devices shown in FIGS. 21–23 is unnecessary.

Figure 24:
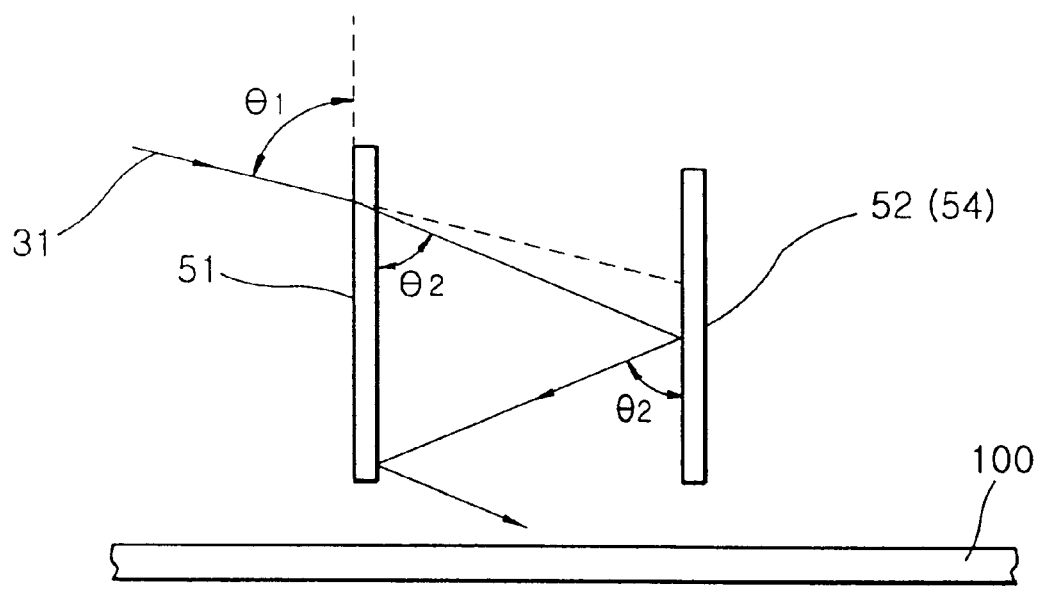
FIG. 24 is a schematic diagram of a ninth embodiment of a device for detecting micro-scratches according to the present invention.

FIG. 24 shows another embodiment of a micro-scratch detection device according to the present invention. In this embodiment, a transparent part of the first mirror 51 extends upward to the extent that the light 31 is incident upon a surface thereof at an incidence angle of θ1. This light passes through the first mirror 51 and is refracted at an angle of refraction θ2 corresponding to the refractive index of the transparent part of the mirror 51. The refracted light then travels between the first mirror 51 and the second (or fourth) mirror 52 (54). Accordingly, the light which travels toward the second (fourth) mirror 52 (54) is reflected several times and then finally reaches the wafer 100 at an angle of incidence of θ2. Note, the angle of incidence θ1 at the upper transparent part of the mirror 51 is preferably designed to correspond to Brewster's angle so that most of the light passes through the upper part of the first mirror 51.

According to the present invention as described above, micro-scratches formed on the surface of a wafer can be successfully detected. In particular, defects such as micro-scratches formed in the surface of a medium layer can be detected regardless of the structure under the medium layer such as a pattern layer.

Finally, although the present invention has been described with reference to the preferred embodiments thereof, it will be apparent to those of ordinary skill in the art that the these embodiments may be changed or modified without departing from the true spirit and scope of the invention as defined by the appended claims.

What is claimed is:

1. A device for detecting micro-scratches in a medium at the surface of a wafer, said device comprising:
    a stage for supporting the wafer;
    an optical system, including a light source, which directs light along an optical path extending to the stage, whereby the light falls at a predetermined angle of incidence upon a wafer supported by the stage;
    scanning means for moving said stage and said optical system relative to one another so that the light is scanned across the surface of a wafer supported by the stage while said predetermined angle of incidence is maintained;
    a signal detection system positioned to receive light which has been reflected, by normal portions of the surface that are flat, at a predetermined angle of reflection substantially identical to said angle of incidence, and generates an electrical signal indicative of the intensity of the reflected light;
    a signal analysis system that ascribes respective values to the electrical signal with reference to different portions of the surface from which the light scanning the surface is reflected, based on the intensity of the light reflected from said portions as represented by the electric signal, and compares the values ascribed to the electric signal in a way that allows a determination of whether micro-scratches are present in the medium to be made; and
    at least one optical element which bends the light as the light travels from the light source to the surface of the wafer and/or from the surface of the wafer to the light detector, whereby the optical path of the light from the light source to the light detector is extended;
    wherein said at least one optical element comprises first and second mirrors extending parallel to each other and perpendicular to an upper wafer-supporting surface of said stage, and another mirror interposed between said first and second mirrors, said mirrors being positioned relative to each other such that said first mirror and said another mirror coact to confine the light to a first space located between said light source and said stage, and said another mirror and said second mirror confine the light to a second space, discrete from said first space and located between said signal detection system and said stage.

2. A device for detecting micro-scratches in a medium at the surface of a wafer, said device comprising:
    a stage for supporting the wafer;
    an optical system, including a light source, which directs light along an optical path extending to the stage, whereby the light falls at a predetermined angle of incidence upon a wafer supported by the stage;
    scanning means for moving said stage and said optical system relative to one another so that the light is scanned across the surface of a wafer supported by the stage while said predetermined angle of incidence is maintained;
    a signal detection system positioned to receive light which has been reflected, by normal portions of the surface that are flat, at a predetermined angle of reflection substantially identical to said angle of incidence, and generates an electrical signal indicative of the intensity of the reflected light;
    a signal analysis system that ascribes respective values to the electrical signal with reference to different portions of the surface from which the light scanning the surface is reflected, based on the intensity of the light reflected from said portions as represented by the electric signal, and compares the values ascribed to the electric signal in a way that allows a determination of whether micro-scratches are present in the medium to be made; and
    at least one optical element which bends the light as the light travels from the light source to the surface of the wafer and/or from the surface of the wafer to the light detector, whereby the optical path of the light from the light source to the light detector is extended;
    wherein said at least one optical element comprises first and second mirrors extending parallel to each other and perpendicular to an upper wafer-supporting surface of said stage;
    wherein said optical system further comprises a third mirror optically interposed between said light source and one of said mirrors so as to reflect light propagating from said light source onto said one of said mirrors at a predetermined angle of incidence;
    said device further comprising a fourth mirror interposed between said first and second mirrors, said first, second and fourth mirrors being positioned relative to each other such that said first and said fourth mirror coact to confine the light to a first space located between said light source and said stage, and said fourth mirror and said second mirror confine the light to a second space, discrete from said first space, located between said signal detection system and said stage.

3. A device for detecting micro-scratches in a medium at the surface of a wafer, said device comprising:
    a stage for supporting the wafer;
    a wafer handler operative to load and unload the wafer onto and from said stage;
    an optical system, including a light source, which directs light along an optical path extending to the stage, whereby the light falls at a predetermined angle of incidence upon a wafer supported by the stage;
    scanning means for moving said stage and said optical system relative to one another so that the light is scanned across the surface of a wafer supported by the stage while said predetermined angle of incidence is maintained;
    a signal detection system positioned to receive light which has been reflected, by normal portions of the surface that are flat, at a predetermined angle of reflection substantially identical to said angle of incidence, and generates an electrical signal indicative of the intensity of the reflected light;
    a signal analysis system that ascribes respective values to the electrical signal with reference to different portions of the surface from which the light scanning the surface is reflected, based on the intensity of the light reflected from said portions as represented by the electric signal, and compares the values ascribed to the electric signal in a way that allows a determination of whether micro-scratches are present in the medium to be made;

a processor operatively connected to said optical and signal analysis control systems; and at least one optical element which bends the light as the light travels from the light source to the surface of the wafer and/or from the surface of the wafer to the light detector, whereby the optical path of the light from the light source to the light detector is extended;

wherein said at least one optical element comprises first and second mirrors extending parallel to each other and perpendicular to an upper wafer-supporting surface of said stage, and another mirror interposed between said first and second mirrors, said mirrors being positioned relative to each other such that said first mirror and said another mirror coact to confine the light to a first space located between said light source and said stage, and said another mirror and said second mirror confine the light to a second space, discrete from said first space and located between said signal detection system and said stage.

4. A device for detecting micro-scratches in a medium at the surface of a wafer, said device comprising:

a stage for supporting the wafer;

a wafer handler operative to load and unload the wafer onto and from said stage;

an optical system, including a light source, which directs light along an optical path extending to the stage, whereby the light falls at a predetermined angle of incidence upon a wafer supported by the stage;

scanning means for moving said stage and said optical system relative to one another so that the light is scanned across the surface of a wafer supported by the stage while said predetermined angle of incidence is maintained;

a signal detection system positioned to receive light which has been reflected, by normal portions of the surface that are flat, at a predetermined angle of reflection substantially identical to said angle of incidence, and generates an electrical signal indicative of the intensity of the reflected light;

a signal analysis system that ascribes respective values to the electrical signal with reference to different portions of the surface from which the light scanning the surface is reflected, based on the intensity of the light reflected from said portions as represented by the electric signal, and compares the values ascribed to the electric signal in a way that allows a determination of whether micro-scratches are present in the medium to be made;

a processor operatively connected to said optical and signal analysis control systems; and at least one optical element which bends the light as the light travels from the light source to the surface of the wafer and/or from the surface of the wafer to the light detector, whereby the optical path of the light from the light source to the light detector is extended;

wherein said at least one optical element comprises first and second mirrors extending parallel to each other and perpendicular to an upper wafer-supporting surface of said stage;

wherein said optical system further comprises a third mirror optically interposed between said light source and one of said mirrors so as to reflect light propagating from said light source onto said one of said mirrors at a predetermined angle of incidence;

said device further comprising a fourth mirror interposed between said first and second mirrors, said first, second and fourth mirrors being positioned relative to each other such that said first and said fourth mirror coact to confine the light to a first space located between said light source and said stage, and said fourth mirror and said second mirror confine the light to a second space, discrete from said first space and located between said signal detection system and said stage.

* * * * *